United States Patent [19]

Borch et al.

[11] Patent Number: 5,233,031
[45] Date of Patent: Aug. 3, 1993

[54] PHOSPHORAMIDATE ANALOGS OF 2'-DEOXYURIDINE

[75] Inventors: Richard F. Borch, Pittsford; Kristin M. Fries, Rochester, both of N.Y.

[73] Assignee: University of Rochester, Rochester, N.Y.

[21] Appl. No.: 763,936

[22] Filed: Sep. 23, 1991

[51] Int. Cl.$^5$ .............................................. C07H 19/00
[52] U.S. Cl. ............................... 536/28.53; 536/28.54; 536/28.55
[58] Field of Search ................... 536/27, 28, 29, 28.4, 536/28.52, 28.54, 28.55

[56] References Cited

U.S. PATENT DOCUMENTS

| | | | |
|---|---|---|---|
| 4,908,356 | 3/1990 | Borch et al. | 514/90 |
| 5,026,838 | 6/1991 | Nojiri et al. | 536/29 |
| 5,118,802 | 6/1992 | Smith et al. | 536/29 |

FOREIGN PATENT DOCUMENTS

| | | |
|---|---|---|
| 0331032 | 9/1989 | European Pat. Off. . |
| 57-128699 | 8/1982 | Japan . |
| WOA8909221 | 10/1989 | PCT Int'l Appl. . |

OTHER PUBLICATIONS

*Journal of Medicinal Chemistry*, vol. 23, No. 6, Jun. 1989, Washington, USA, pp. 661-665, J. S. Park et al., "Oxime and Dithiolane Deriuvatives of 5-Formyl-2'-Deoxyuridine and Their 5'-Phosphates: Antiviral Effects and Thymidylate Synthetase Inhibition" (see whole document).

*Chemical Abstracts*, vol. 98, No. 1, Jan. 3, 1983, Columbus, Ohio, US, Abstract No. 4751s, "Pharmacologically Active 5-Fluorouracil Derivatives" p. 428, column 2, see abstract (JP A 57 128 699, Tokyo Kinzoku Kogyo Co., Ltd.), Aug. 10, 1982.

F. Cortese, *Org. Syn.*, 18, 13 (1938).
K. Fries et al., *J. Med. Chem.*, 34, 565 (1991).
R. Langenbach et al., *Biochem. Biophys. Res. Comm.*, 48, 1565 (1972).
A. Meyers et al., *J. Org. Chem.*, 38, 36 (1973).
C. Moertel, *New Eng. J. Med.*, 299, 1949 (1978).
D. Santi et al., *Biochem.*, 13, 471 (1974).
A. Sartorelli and D. Johns, editors, in *Antineoplastic and Immunosuppressive Drugs*, Springer-Verlag, NY and Berlin, at pp. 1090-1091 (1974-75).
Aldrich Chem. Co. 1992 Catalog (p. 1275).

*Primary Examiner*—Johnnie R. Brown
*Assistant Examiner*—J. Oliver Wilson
*Attorney, Agent, or Firm*—Merchant, Gould, Smith, Edell, Welter & Schmidt

[57] ABSTRACT

The present invention provides a series of cytotoxic phosphoramidate analogs of 5-fluoro-2'-deoxyuridine of the general formula (I):

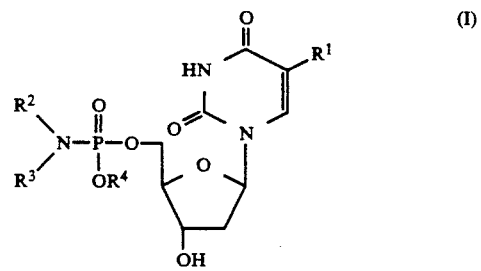

wherein $R^1$ is H, F or $(C_1-C_4)$alkyl; $R^2$ is $CH_2CH_2X$ wherein X is Cl, Br, I or p-toluenesulfonyl; $R^3$ is $(C_1-C_4)$alkyl or $CH_2CH_2X$ wherein X is Cl, Br, I or p-toluenesulfonyl; or wherein $R^2$ and $R^3$, taken together with the N atom, can be a 5- or 6-membered heterocyclic ring which is aliphatic or aliphatic interrupted by a ring oxygen or a second ring nitrogen; $R^4$ is H, one equivalent of a pharmaceutically-acceptable cation or (4,4,6-trimethyltetrahydro-1,3-oxazin-2-yl)ethyl, and the pharmaceutically-acceptable salts thereof.

10 Claims, 1 Drawing Sheet

FIG. 1

PHOSPHORAMIDATE ANALOGS OF 2'-DEOXYURIDINE

BACKGROUND OF THE INVENTION

The present invention was made with the support of National Cancer Institute grants CA34619 and CA11198. The U.S. Government has certain rights in the invention.

5-Fluorouracil (5-FU) is the antineoplastic agent of choice for the treatment of carcinoma of the pancreas, and, in combination with semustine, is widely used to treat colorectal cancer and gastric cancer. Fluorouracil is also used topically in the treatment of precancerous dermatoses, especially actinic keratosis, for which it is the treatment of choice when multiple lesions occur.

5-FU is a congener of uracil that acts both as a surrogate and as an antimetabolite of that nucleotide. Its metabolite, 5-fluorodeoxyuridine-5'-monophosphate (F-dUMP) is a potent inhibitor of thymidylate synthetase, thus blocking the synthesis of thymidylic acid and hence of DNA. The analog 2'-deoxy-5-fluorouridine has been used to treat adenocarcinoma metastatic to the liver. Despite the potency of 5-FU, low response rates, low therapeutic indices, and the development of resistance represent major problems in the clinical application of this drug and its analogs.

Therefore, a need exists for analogs or prodrugs of 5-FU that are both readily taken up by tumor cells while retaining the ability to inhibit thymidylate synthetase.

SUMMARY OF THE INVENTION

The present invention provides a series of phosphoramidate analogs of 5-fluoro-2'-deoxyuridine of the general formula (I):

wherein $R^1$ is H, F or $(C_1-C_4)$alkyl; $R^2$ is $CH_2CH_2X$ wherein X is Cl, Br, I or p-toluenesulfonyl; $R^3$ is $(C_1-C_4)$alkyl or $CH_2CH_2X$ wherein X is Cl, Br, I or p-toluenesulfonyl; or wherein $R^2$ and $R^3$, taken together with the N atom, can be a 5- or 6-membered heterocyclic ring which is aliphatic or aliphatic interrupted by a ring oxygen or a second ring nitrogen; $R^4$ is H, one equivalent of a pharmaceutically-acceptable cation or (4,4,6-trimethyltetrahydro-1,3-oxazin-2-yl)ethyl, and the pharmaceutically-acceptable salts thereof.

Preferably $R^1$ is F, H, or $CH_3$, most preferably $R^1$ is F. Preferably $R^4$ is the moiety (4,4,6-trimethyltetrahydro-1,3-oxazin-2-yl)ethyl. Compounds containing this moiety can readily cross cell membranes and are intracellularly converted into phosphoramidate derivatives wherein $R^4$ is H. Compounds of the present invention wherein $R^4$ is (4,4,6-trimethyltetrahydro-1,3-oxazin-2-yl)ethyl are shown on Table I, below.

TABLE I

| Cpd No. | $R^1$ | $R^2$ | $R^3$ | LC-99 $(\mu M)^a$ |
|---|---|---|---|---|
| 1a | F | $CH_2CH_2Br$ | $CH_3$ | 100 |
| 1b | F | $CH_2CH_2OTs$ | $CH_3$ | 156 |
| 1c | F | $CH_2CH_2Cl$ | $CH_3$ | 308 |
| 1d | F | $CH_2CH_2I$ | $CH_3$ | 95 |
| 1e | F | —$CH_2CH_2OCH_2CH_2$— | | 216 |
| 2 | H | —$CH_2CH_2OCH_2CH_2$— | | 190 |
| 3 | $CH_3$ | —$CH_2CH_2OCH_2CH_2$— | | 152 |
| 4 | F | —$(CH_2)_5$— | | 98 |
| 5 | H | $CH_2CH_2Br$ | $CH_3$ | 318 |
| 6 | H | $CH_2CH_2Br$ | $CH_2CH_2Br$ | 150 |
| 7 | $CH_3$ | $CH_2CH_2Br$ | $CH_3$ | 165 |
| 8 | $CH_3$ | $CH_2CH_2Br$ | $CH_2CH_2Br$ | 120 |
| 9 | F | $CH_2CH_2Br$ | $CH_2CH_2Br$ | 90 |

$^a$Concentration of compound required to kill 99% of B16 melanoma cells in a clonogenic assay. Cells were treated with the compound for 2 hr.

It is believed that the present compounds exhibit antitumor and/or antiviral activity at least in part via their ability to inhibit the enzyme thymidylate synthase (TS). Compounds wherein at least one of $R^2$ or $R^3$ is $CH_2CH_2X$, wherein X is a leaving group such as Cl, Br, I, p-toluenesulfonyl (OTs) or a similar leaving group, can function as irreversible inhibitors of TS, while compounds wherein $R^2$ and $R^3$ taken together with the N atom form a 5-6 membered ring can be hydrolyzed intracellularly to release the bioactive nucleotide $NucOPO_3^{-2}$ wherein Nuc is the corresponding nucleoside. The inhibition of TS by these analogs is reversible.

Analogs of the general formula $NucOP(O)(NR^2R^3)(O^-)$ are also within the scope of the invention, since they are believed to represent the reactive intermediates which are formed in situ following uptake of the corresponding oxazinylethyl-substituted compounds by the target cells.

The present invention is also directed to a method for the inhibition of thymidylate synthetase (TS) by contacting TS with an effective inhibiting amount of one or more compounds of formula I, either in vitro or in vivo. When administered to mammals in vivo, the compounds of formula I can be used to treat conditions which can be ameliorated by the inhibition of TS activity. Such conditions include cancers which respond to 5-fluorouracil (5-FU) treatment, such as gastrointestinal cancer, pancreatic cancer, colorectal cancer, malignant insulinoma, primary hepatocellular carcinoma, prostate cancer, bladder cancer, endometrial carcinoma, cervical cancer, breast cancer, ovarian cancer and the like. The present compounds can also act to inhibit viral replication in vivo or in vitro. Generally, the compounds of formula I are about 10–100 times more active than 5-FU, while exhibiting fewer side effects.

The present invention is also directed to novel intermediates which can be employed to prepare the compounds of formula I.

DETAILED DESCRIPTION OF THE INVENTION

Figure 1:
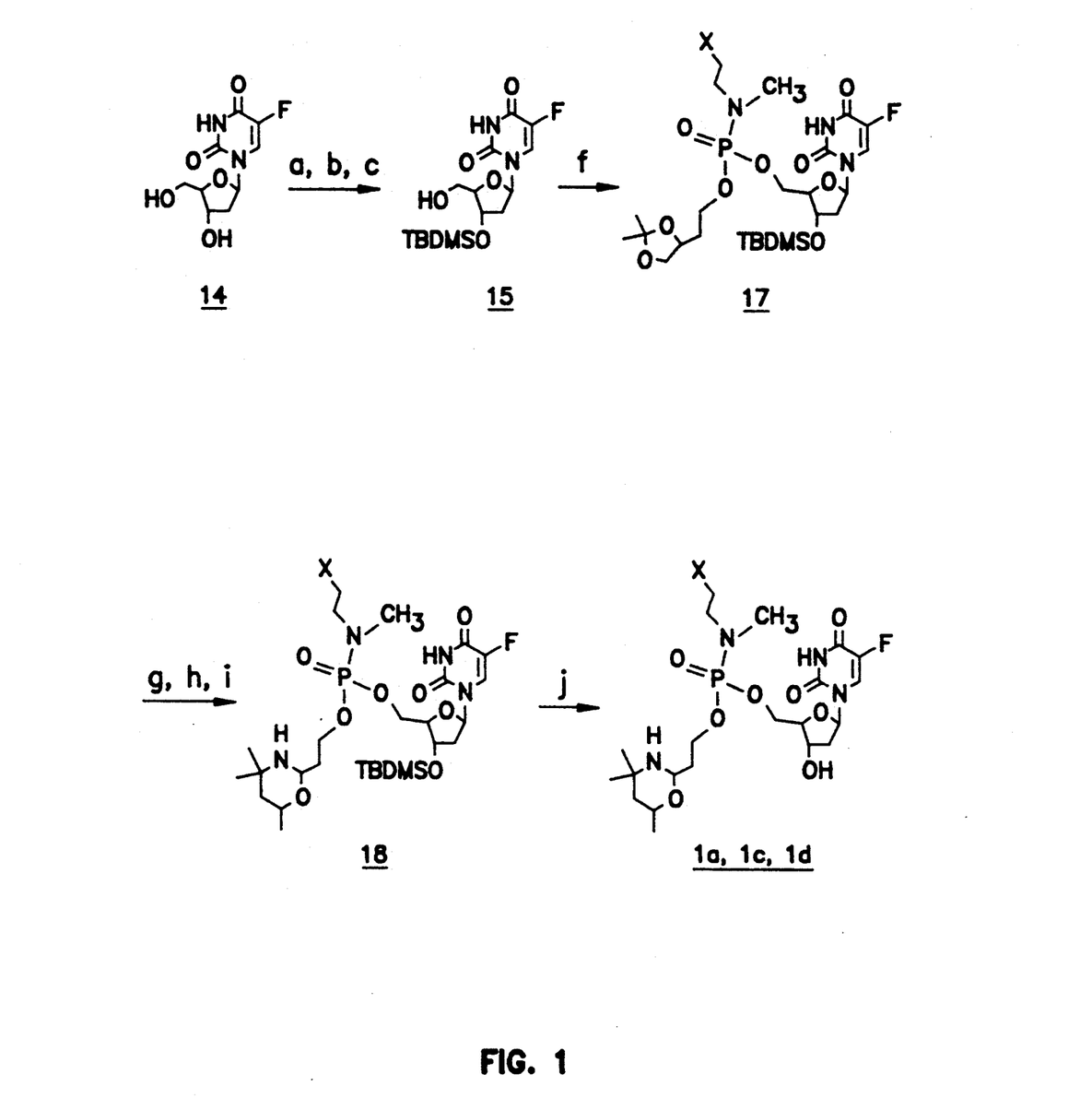

Compounds 1a-d are prepared from 5-fluoro-2'-deoxyuridine as outlined in FIG. 1, using the reagents and reaction conditions summarized in Table II, below.

TABLE II

| Step | Reaction Conditions | Product |
|------|---------------------|---------|
| a | Ph₃CCl, dimethylaminopyridine, pyridine, 80° C., 30 min | — |
| b | t-butyldimethylsilylchloride, imidazole, DMF, 18 hr, 25° C. | — |
| c | HOAc—H₂O, 30 min, reflux | 15 |
| f | Lithium diisopropylamide, then add to 16a-c, THF, 0° to 25° C., 18 hr. | 17 |
| g | HOAc—H₂O, 80° C., 30 min; then NaOH | |
| h | NaIO₄, pH = 5.0, THF | |
| i | 4-Methyl-4-amino-2-pentanol, 3Å molec. sieves, CH₂Cl₂ | 18 |
| j | Bu₄NF, THF, 0° | 1a–d |

To prepare compounds 1a, 1c and 1e, step f is carried out using intermediates 16a-c, respectively, which have the general formula (16):

wherein X is Cl, Br or I, respectively.

Generally, the 3'-protected nucleoside 15 was prepared by treating the 2'-deoxynucleoside, 14 sequentially with triphenylmethyl chloride and t-butyldimethylsilyl chloride, followed by detritylation. The phosphorylating agent was prepared by reaction of phosphorus oxychloride with the appropriate amine salt followed by treatment with the lithium salt of 4-(2-hydroxyethyl)-2,2-dimethyl-1,3-dioxolane. The protected nucleoside 15 was then converted to its alkoxide and phosphorylated with 16 to give 17. The acetonide was hydrolyzed, the resulting diol was cleaved with sodium periodate, and the resulting aldehyde was trapped with 4-methyl-4-amino-2-pentanol to give 18. Finally, the 3'-protecting group was removed to give the 2'-deoxynucleotide phosphoramidates 1a, 1c or 1d.

Tosyl analog 16 was prepared by reacting 17, X=Br with silver tosylate in acetonitrile at reflux for 3 hr to yield 17, X=OTs, which was further reacted as described above.

Morpholino analog 1e was prepared by replacing intermediate 16 with 2-(2,2-dimethyl-1,3-dioxolan-4-yl)ethyl-morpholino-phosphoramidyl chloride, which was in turn prepared by reacting phosphorus oxychloride sequentially with morpholine and 4-(2-hydroxyethyl)-2,2-dimethyl-1,3-dioxolane. Morpholine can be replaced with other heterocyclic ring compounds, such as piperazine and piperidine to afford compounds of formula I wherein $R^2$ and $R^3$ taken together with N are a 5- or 6-membered heterocyclic ring.

Useful dosages of the compounds of formula I can be determined by comparing their in vitro activity, and in vivo activity in animal models, to that of an equivalent dosage of 5-fluorouracil of or of 2'-deoxy-5-fluorouridine, both of which are currently employed in the treatment of human cancers. For example, a compound of formula I that is 10-20 times more potent than 5-FU against a particular cancer, such as those discussed above, may be administered intravenously in a single unit dose of about 0.75-1.5 mg/kg once a week, for as long as clinical improvement is evident. The dosage can be adjusted weekly according to the patient's tolerance. The compounds of the present invention can also be administered orally, as in capsules or tablets. The present compounds can also be applied topically, e.g., in a 1-5% cream or in a 1-5% solution, in combination with a semi-solid emulsified cream base, or in combination with a pharmaceutically-acceptable liquid vehicle.

Pharmaceutically-acceptable cations include alkali metal salts ($Li^+$, $Na^+$, $K^+$) as well as $NH_4^+$ and other nontoxic ammonium salts. Pharmaceutically-acceptable salts of the compounds of formula I include nontoxic amine acid addition salts of inorganic acids (HCl, $H_2SO_4$, $H_3PO_4$) and organic acids, e.g., citrates, tartrates, gluconates, polygluconates, malates and the like.

The present compounds of formula I include both the racemic (dl), partially-resolved (optically-active) mixtures of stereoisomers or the fully resolved forms. Typically, the 1' and 4' bonds of the oxocyclopentane ring will be beta (or above the plane of the ring) and the 3'-hydroxy hydroxy group will be alpha (or below the plane of the ring), as depicted hereinabove.

The invention will be further described by reference to the following detailed examples in which ⁻P NMR spectra were recorded on a Bruker WP-270 SY instrument equipped with a VSP multinuclear probe tuned for 109.368 MHz using 10 mm sample tubes, 5000 Hz spectral width, and 64 acquisitions. Broadband gated decoupling was used, and chemical shifts are reported in parts per million from 5% triphenylphosphine oxide in toluene-d₈ as a coaxial reference. ¹H NMR spectra were recorded on the same instrument using 5 mm sample tubes and 32 acquisitions. Chemical shifts are reported in parts per million from tetramethylsilane.

Elemental analyses were performed by Galbraith Laboratories, Knoxville, Tenn. IR spectra were recorded on a Perkin Elmer 1310 Infrared Spectrometer. Melting points were determined on a Mel-Temp apparatus and are uncorrected.

All chromatography refers to flash chromatography over silica gel, and all organic solvents were distilled prior to use unless otherwise specified.

EXAMPLE 1

N-Methyl-N-(2-bromoethyl)amine, hydrobromide salt

This compound was prepared as described previously by F. Cortese, Org. Syn., 18, 13 (1938), on a 133 mmol scale and isolated as a white solid (20.36 g, 70%): mp 66°-74° C.; ¹H NMR (CDCl₃) 3.83(t, 2H, J=6.67 Hz), 3.47(t, ₂H, J=6.35 Hz), 2.82(s, 3H)ppm; IR (KBr) 3410, 2960, 2750, 2410, 1630, 1590, 1470, 1440, 1310, 1260, 945, 910, 1060, 1015, 960, 945, 870, 805 cm⁻¹.

EXAMPLE 2

N-Methyl-N-(2-chloroethyl)amine, hydrochloride salt

Hydrogen chloride was bubbled into a stirred solution of 2-(methylamino)ethanol (10 g, 133 mmol) in CH₂Cl₂ (25 ml) until the mixture turned wet litmus paper red. The mixture was cooled to 0° C., and thionyl chloride (15.82 g, 133 mmol) was added dropwise. The mixture was allowed to stir overnight at room temperature. The solvent was removed under reduced pressure to give product as a white solid (16.60 g, 96% yield): mp 95°–100° C.; $^1$H NMR (DMSO-d$_6$) 4.00(t, 2H, J=6.28 Hz), 3.36(t, 2H, J=6.29 Hz), 2.81(s, 3H)ppm; IR (KBr) 3400, 2960, 2750, 2420, 1730, 1580, 1460, 1390, 1310, 1270, 1200, 1150, 1165, 1005, 990, 900, 860, 710 cm$^{-1}$.

EXAMPLE 3

N-Methyl-N-(2-iodoethyl)amine, hydriodide salt

This compound was prepared analogously to the bromo analog of Example 1, on a 133 mmol scale. The product was isolated as an off white solid (38.73 g, 93% yield): mp 134°–136° C.; $^1$H NMR (CDCl$_3$) 3.32(m, 4H), 2.60(s, 3H)ppm; IR (KBr) 3100, 3000, 2960, 2860, 2750, 2710, 2470, 1560, 1460, 1450, 1415, 1395, 1350, 1190, 1135, 1100, 1070, 1050, 1000, 975, 955, 910, 835, 850 cm$^{-1}$.

EXAMPLE 4

4-(2-Hydroxyethyl)-2,2-dimethyl-1,3-dioxolane

Butane-1,2,4-triol (5.0 g, 47 mmol) was dissolved in MeOH (5 ml). Acetone (20 ml), MgSO$_4$ (ca. 500 mg), and para-toluene sulfonic acid (p-TsOH) (catalytic amount) were added, and the mixture was allowed to stir for 5 days at room temperature. The mixture was filtered and the filtrate concentrated under reduced pressure. Methylene chloride (CH$_2$Cl$_2$) (20 ml) and water (20 ml) were added, the layers were separated, and the organic layer was washed with water (2×20 ml). The organic layer was dried (MgSO$_4$), filtered, and the filtrate concentrated under reduced pressure to afford the product as a clear oil (5.15 g, 75%): $^1$H NMR (CDCl$_3$) 4.23(dt, 1H, J=6.86 Hz), 4.04(t, 1H, J=6.06 Hz), 3.72(m, 2H), 3.54(t, 1H, J=7.72 Hz), 2.55(broad s, 1H), 1.77(dt, 2H, J=6.67 Hz), 1.34(d, 6H, J=15.68 Hz)ppm; IR (neat) 3420, 2980, 2930, 2870, 1710, 1455, 1370, 1250, 1215, 1155, 1055, 855, 732 cm$^{-1}$.

EXAMPLE 5

4-Methyl-4-amino-2-pentanol 5,6-Dihydro-2,4,4,6-tetramethyl-4H-1,3-oxazine (10 g, 70 mmol) was refluxed in 80 ml of 10% aqueous NaOH for 8.5 hr. The mixture was allowed to cool to room temperature and was then saturated with NaCl and extracted with ether (5×30 ml). The ether extracts were combined and dried over solid KOH. The solvent was removed under reduced pressure to afford the product as an oil (7.30 g, 89%): $^1$H NMR (CDCl$_3$) 4.06(m, 1H), 1.34(d, 2H, J=5.54 Hz), 1.15(s, 6H), 1.09(d, 3H, J=7.17 Hz)ppm; IR (neat) 3340, 3280, 2960, 2920, 2890, 2870, 1600, 1465, 1440, 1380, 1365, 1335, 1300, 1260, 1190, 1170, 1130, 1100, 1050, 1000, 970, 900, 875, 835, 760 cm$^{-1}$.

EXAMPLE 6

3'-O-t-Butyldimethylsilyl-5-fluoro-2'-deoxyuridine (15)

To a solution of 5-fluoro-2'-deoxyuridine (14, 1.00 g, 4.06 mmol) in pyridine (7 ml) was added triphenylmethyl chloride (1.25 g, 4.47 mmol) and dimethylaminopyridine (0.4 g, 3.05 mmol). The mixture was allowed to stir at 80° C. for 30 min. The pyridine was removed under reduced pressure and the residue dissolved in DMF (4 ml). Imidazole (0.67 g, 9.77 mmol) and t-butyldimethylsilyl chloride (0.74 g, 4.88 mmol) were added, and the mixture was allowed to stir overnight at room temperature. The DMF was removed under pressure, and the residue was dissolved in 80% aqueous acetic acid (5 ml). The mixture was allowed to reflux for 30 min, cooled, and neutralized with NaOH. The mixture was lyophilized, and the residue was purified by chromatography (1:1 EtOAc:hexanes) to give 15 as a white solid (709 mg, 48%): mp 138°–142° C.; R$_f$ 0.65 (1:9 MeOH:CH$_2$Cl$_2$); $^1$H NMR (CDCl$_3$) 7.98(d, 1H, J=6.39 Hz), 6.23(t, 1H, J=6.78 Hz), 4.49(dt, 1H, J=5.56 Hz), 3.98(m, 2H), 3.84(m, 1H), 2.26(m, 2H), 0.90(s, 9H), 0.10(s, 6H); IR (KBr) 3460, 3190, 3080, 3050, 2930, 2860, 1720, 1655, 1490, 1475, 1445, 1400, 1335, 1250, 1190, 1120, 1095, 1030, 1005, 950, 910, 835, 760, 700, 670, 640 cm$^{-1}$.

EXAMPLE 7

[2-(2,2-dimethyl-1,3-dioxolan-4-yl)ethyl]-N-methyl-N-(2-bromoethyl)phosphoramidoyl chloride (16a)

Triethylamine (12.24 g, 121 mmol) was added dropwise to a stirred solution of N-methyl-N-bromoethylamine.HBr (12.04 g, 55 mmol) and phosphorus oxychloride (8.44 g, 55 mmol) in CH$_2$Cl$_2$ (100 ml) at 0° C. under N$_2$. The mixture was allowed to stir overnight and then poured over ice. The layers were separated, and the aqueous layer was extracted with CH$_2$Cl$_2$ (3×100 ml). The organic layers were combined and dried (MgSO$_4$). The filtrate was concentrated under reduced pressure and the residue purified by chromatography (1:4 EtOAc:hexanes) to give N-methyl-N-(2-bromoethyl)phosphoramidic dichloride as an oil (13 g, 93%): R$_f$0.67 (1:4 EtOAc:hexanes); $^1$H NMR (CDCl$_3$) 3.65(dt, 2H, J=14.10 Hz), 3.50(t, 2H, J=6.52 Hz), 2.93(d, 3H, J=15.46 Hz)ppm; $^{31}$P NMR (CDCl$_3$) −6.57 ppm; IR (neat) 2980, 2940, 2880, 1740, 1450, 1370, 1340, 1280, 1250, 1210, 1105, 1050, 1005, 980, 975, 940, 915, 865, 755, 700 cm$^{-1}$.

Butyllithium (10.8 ml, 21.60 mmol, 2.0M) was added dropwise at 0° C. to a stirred solution of 4-(2-hydroxyethyl)-2,2-dimethyl-1,3-dioxolane (2.87 g, 19.60 mmol) and a crystal of 4-phenylazodiphenylamine indicator in THF (7 ml) under N$_2$. The resulting solution was added dropwise at −78° C. to a stirred solution of N-methyl-N-(2-bromoethyl) phosphoramidic dichloride (5.00 g, 19.60 mmol) in THF (10 ml) under N$_2$. The mixture was allowed to stir under N$_2$ at −78° C. for 3 hr, at which time the purple mixture turned yellow. The mixture was warmed to room temperature and the solvent removed under reduced pressure. The residue was purified by chromatography (1:4 EtOAc: hexanes) and the product 16a isolated as an oil (4.77 g, 67%): R$_f$0.61 (1:1 EtOAc:hexanes); $^1$H NMR (CDCl$_3$) 4.26(dt, 2H, J=8.44 Hz), 4.17(t, 1H, J=6.53 Hz), 4.06(t, 1H, J=7.06 Hz), 3.54(t, 1H, J=7.10 Hz), 3.44(m, 4H), 2.76(d, 3H, J=12.76 Hz), 1.95(dt, 2H, J=6.24 Hz), 1.67(d, 6H, 15.63 Hz); $^{31}$P NMR (CDCl$_3$) −8.07 ppm.

EXAMPLE 8

3'-O-t-Butyldimethylsilyl-5-fluoro-2'-deoxy-5'-uridyl-[2-(2,2-dimethyl-1,3-dioxolan-4-yl)ethyl]-N-methyl-N-(2-bromoethyl)phosphoramidate (17, X=Br)

Lithium diisopropylamide was prepared by adding n-butyllithium (1.38 ml, 2.75 mmol, 2.0M) to a stirred solution of diisopropylamine (0.39 ml, 2.75 mmol) in THF (1 ml) at 0° C. under N$_2$. The mixture was allowed to stir at 0° C. for 10 min. This solution was added dropwise to a stirred solution of 15 (0.45 g, 1.25 mmol) in THF (5 ml) at 0° C. under N$_2$. This alkoxide solution was then added dropwise to a stirred solution of 16a (0.4 g, 1.25 mmol) in THF (5 ml) at 0° C. under N$_2$, and stirring was continued overnight at room temperature. The solvent was then removed under reduced pressure and the residue purified by chromatography (EtOAc) to give 17, X=Br (0.72 g, 71%): R$_f$ 0.71 (1:9 MeOH:CH$_2$Cl$_2$); $^1$H NMR (CDCl$_3$) 7.82(d, ½H, J=6.41 Hz), 7.77(d, ½H, J=6.25 Hz), 6.27(m, 1H), 4.44(m, 1H), 4.11(m, 7H), 3.56(5, 1H, J=7.37 Hz), 3.46(m, 4H), 2.72(d, 3H, J=9.34 Hz), 2.30(m, 1H), 2.03(m, 1H), 1.93(m, 2H), 1.36(d, 6H, J=13.89 Hz), 0.87(s, 9H), 0.08(s, 6H)ppm; $^{31}$P NMR (CDCl$_3$) −14.30, −14.50 ppm.

EXAMPLE 9

3'-O-t-Butyldimethylsilyl-5-fluoro-2'-deoxy-5'-uridyl-[2-(4,4,6-trimethyltetrahydro-1,3-oxazin-2-yl)ethyl]-N-methyl-N-(2-bromoethyl)phosphoramidate (18, X=Br)

Compound 17, X=Br (340 mg, 0.50 mmol) was dissolved in 80% aqueous acetic acid (2 ml), heated to 80° C. for 30 min, cooled, and neutralized with NaOH. The solution was lyophilized, the residue taken up in THF, the salts removed by filtration, and the residue concentrated under reduced pressure to afford the corresponding diol as an oil (270 mg, 83%): R$_f$ 0.54 (1:9 MeOH:CH$_2$Cl$_2$); $^{31}$P NMR −13.53, −13.93, −14.06 ppm. To a solution of the diol (220 mg, 0.35 mmol) in THF (3 ml) was added NaIO$_4$ (80 mg, 0.39 mmol) in acetate buffer (3 ml, 1M in H$_2$O, pH=5.0). The mixture was allowed to stir for 10 min, and the THF was then removed under reduced pressure. The mixture was lyophilized, the residue taken up in THF, and the salts filtered, and the filtrate concentrated under reduced pressure. The residue was dissolved in CH$_2$Cl$_2$ (3 ml) and the amino alcohol of Ex. 5 (40 mg, 0.35 mmol) in CH$_2$Cl$_2$ (2 ml) was added. The mixture was allowed to stir over 3 Å molecular sieves for 15 min. The sieves were removed and the solvent removed under reduced pressure. The residue was purified by chromatography (2% MeOH:EtOAc) to afford 18, X=Br (161 mg, 65%): R$_f$0.69 (1:9 MeOH:CH$_2$Cl$_2$); $^1$H NMR (CDCL$_3$) 7.78(d, ½H, J=6.07 Hz), 7.73(d, ½H, J=6.07 Hz), 6.23(m, 1H), 4.40(m, 2H), 4.04(m, 5H), 3.74(m, 1H), 3.43(m, 4H), 2.69(d, 3H, J=9.17 Hz), 2.27(m, 1H), 2.01(m, 1H), 1.87(m, 2H), 1.41(d, 1H, J=13.24 Hz), 1.14(m, 10H), 0.85 (s, 9H), 0.05(s, 6H); $^{31}$P NMR (CDCl$_3$) −14.30, −14.52 ppm.

EXAMPLE 10

5-Fluoro-2'-deoxy-5'-uridyl-[2-(4,4,6-trimethyltetrahydro-1,3-oxazin-2-yl)ethyl]-N-methyl-N-(2-bromoethyl)-phosphoramidate (1a)

Tetrabutylammonium fluoride (0.15 ml, 0.15 mmol, 1.0M in THF) was added at 0° C. to a stirred solution of 18, X=Br (0.105 g, 0.15 mmol) in THF (3 ml). The mixture was allowed to stir for 20 min at 0° C. The solvent was removed under reduced pressure and the residue purified by chromatography (3% MeOH:EtOAc) to afford 1a (33 mg, 37%): R$_f$ 0.40 (1:9 MeOH:CH$_2$Cl$_2$); $^1$H NMR (CDCl$_3$) 7.79(m, 1H), 6.22(m, 1H), 4.51(m, 1H), 4.45(m, 1H), 4.25(m, 5H), 3.74(m, 1H), 3.48(m, 4H), 2.72(d, 3H, J=9.54 Hz), 2.45(m, 1H), 2.16(m, 1H), 1.92(m, 2H), 1.43(d, 1H, J=11.60 Hz), 1.10(m, 9H), 0.91(d, 1H, J=12.00 Hz)ppm; $^{31}$P NMR (CDCl$_3$) −13.29, −13.65, −13.69, −13.81 ppm; IR (neat) 3370, 3080, 2960, 2920, 1710, 1660, 1470, 1400, 1350, 1260, 1230, 1090, 1030, 975, 900, 870, 800, 760, 730 cm$^{-1}$; LSIMS m/e 601(M+H)$^+$, 623(M+Na)$^+$.

EXAMPLE 11

3'-O-t-Butyldimethylsilyl-5-fluoro-2'-deoxy-5'-uridyl-[2-(2,2-dimethyl-1,3-dioxolan-4-yl)ethyl]-N-methyl-N-(2-tosylethyl)phosphoramidate (17, X=OTs)

Silver tosylate (1.09 g, 3.91 mmol) was added to a solution of 17, X=Br (0.67 g, 0.98 mmol) in CH$_3$CN (2.5 ml). The mixture was refluxed for 3 hr. The mixture was cooled, filtered, and the solvent removed under reduced pressure to afford 17, X=OTs as an oil (0.70 g, 92%): R$_f$0.75 (1:9 MeOH:CH$_2$Cl$_2$); $^1$H NMR (CDCl$_3$) 7.74(m, 3H), 7.31(d, 2H, J=8.04 Hz), 6.24(m, 1H), 4.41(m, 1H), 4.00(m, 9H), 3.52(t, 1H, J=7.31), 3.28(m, 2H), 2.65(d, 3H, J=9.34 Hz), 2.40(s, 3H), 2.22(m, 1H), 2.02(m, 1H), 1.88(m, 2H), 1.32(d, 6H, J=16.24 Hz), 0.84(s, 9H), 0.05(s, 6H)ppm; −P NMR (CDCl$_3$) −13.38, −12.92 ppm; LSIMS m/e 780.2(M+H)$^+$, 802.2(M+Na)$^+$.

EXAMPLE 12

3'-O-t-Butyldimethylsilyl-5-fluoro-2'deoxy-5'-uridyl-[2-(4,4,6-trimethyltetrahydro-1,3-oxazin-2-yl)ethyl]-N-methyl-N-(2-tosylethyl)phosphoramidate (18, X=OTs)

This compound was prepared as described for 18, X=Br (0.90 mmol scale). The crude product was purified by chromatography (2% MeOH:EtOAc) to afford 18, X=OTs (333 mg, 46%): R$_f$ 0.73 (1:9 MeOH:CH$_2$Cl$_2$); $^1$H NMR (CDCl$_3$) 7.86(d, ½H, J=6.16 HZ), 7.77(m, 2½H), 7.34(d, 2H, J=7.81 HZ), 6.25(m, 1H), 4.44(m, 2H), 4.11(m, 5H), 3.93(m, 1H), 3.74(m, 2H), 3.42(m, 2H), 2.68(d, 3H, J=9.42 HZ), 2.44(s, 3H), 2.26(m, 1H), 2.03(m, 1H), 1.90(m, 2H), 1.42(m, 1H), 1.13(m, 10H), 0.88(s, 9H), 0.08(s, 6H)ppm; $^{31}$P NMR (CDCl$_3$) −14.13, −14.36 ppm.

EXAMPLE 13

5-Fluoro-2'-deoxy-5'-uridyl-[2-(4,4,6-trimethyltetrahydro-1,3-oxazin-2-yl)ethyl]-N-methyl-N-(2-tosylethyl)-phosphoramidate (1b)

This compound was prepared as described for 1a (0.41 mmol scale). The crude product was purified by chromatography (3% MeOH:EtOAc) to give 1b (37 mg, 13% yield): R$_f$0.42 (1:9 MeOH:CH$_2$Cl$_2$); $^1$H NMR (CDCl$_3$) 7.76(m, 3H), 7.36 (d, 2H, J=7.75 HZ), 6.20(m, 1H), 4.48(m, 2H), 4.17(m, 6H), 3.76(m, 2H), 3.30(m, 2H), 2.69(d, 3H, J=9.80 Hz), 2.45(s, 3H), 2.22(m, 1H), 2.05(m, 1H), 1.94(m, 2H), 1.40(d, 1H, J=12.99 Hz), 1.15(m, 9HO, 0.10(d, 1H, J=14.60 Hz)ppm; $^{31}$P NMR (CDCl$_3$) −13.30, −13.58 ppm; LSIMS calcd for MH$^+$693.2371; found 693.2385.

EXAMPLE 14

[2-(2,2-dimethyl-1,3-dioxolan-4-yl)ethyl-N-methyl-N-(2-chloroethyl)phosphoramidoyl chloride (16b)

This compound was prepared from N-methyl-N-chloroethylamine.HCl via N-methyl-N-(2-chloroethyl)-phosphoramidic dichloride, as described for 16a (14 mmol scale). The crude residue was purified by chromatography (1:4 EtOAc:hexanes) to give 16b as an oil (2.72 g, 61%): R$_f$0.75 (1:1 EtOAc:hexanes); $^1$H NMR (CDCl$_3$) 4.22(m, 4H), 3.60(m, 3H), 3.42(m, 2H), 2.80(d, 3H, J=12.85 Hz), 1.99(dt, 2H, J=6.11 Hz), 1.36(d, 6H, J=15.82 Hz)ppm; −P NMR (CDCl$_3$) −7.69, −7.92 ppm (1:1 ratio of diastereomers).

EXAMPLE 15

3'O-t-Butyldimethylsilyl-5-fluoro-2'-deoxy-5'-uridyl-[2-(2,2-dimethyl-1,3-dioxolan-4-yl)ethyl]-N-methyl-N-(2-chloroethyl)phosphoramidate (17, X=Cl)

This compound was prepared as described for 17, X=Br (1.39 mmol scale) using 16b. The crude residue was purified by chromatography (EtOAc) to give 17, X=Cl (725 mg, 81%): $R_f$ 0.75 (1:9 MeOH:$CH_2Cl_2$); $^1$H NMR ($CDCl_3$) 7.84(d, ½H, J=6.48 Hz), 7.77(d, ½H, J=6.32 Hz), 6.27(m, 1H), 4.43(m, 1H), 4.11(m, 7H), 3.59(m, 3H), 3.37(m, 2H), 2.72(d, 3H, J=8.61 HZ), 2.28(m, 1H), 2.05(m, 1H), 1.92(m, 2H), 1.35(d, 6H, J=16.21 HZ), 0.88(s, 9H), 0.08(s, 6H)ppm; $^{31}$P NMR ($CDCl_3$) −14.19, −14.44 ppm (1:1 ratio of diastereomers); LSIMS m.e/ 644.2(M+H)$^+$, 666.1(M+Na)$^+$.

EXAMPLE 16

3'-O-t-Butyldimethylsilyl-5-fluoro-2'-deoxy-5'-uridyl-[2-(4,4,6-trimethyltetrahydro-1,3-oxazin-2-yl)ethyl]-N-methyl-N-(2-chloroethyl)phosphoramidate (18, X=Cl)

This compound was prepared as described for 18, X=Br (1.13 mmol scale). The crude residue was purified by chromatography (2% MeOH:EtOAc) to afford 18, X=Cl (217 mg, 30%): $R_f$ 0.73 (1:9 MeOH:$CH_2Cl_2$); $^1$H NMR ($CDCl_3$) 7.81(d, ½H, J=6.32 Hz), 7.75(d, ½H, J=6.30 Hz), 6.26(m,1H), 4.40(m, 2H), 4.05(m, 5H), 3.74(m, 1H), 3.60(m, 2H), 3.36(m, 2H), 2.71(d, 3H, 9.38 Hz), 2.29(m, 1H), 2.03(m, 1H), 1.94(m, 2H), 1.42(d, 1H, J=12.77 Hz), 1.13(m, 10H), 0.86(s, 9H), 0.05 (s, 6H)ppm; $^{31}$P NMR ($CDCl_3$) −14.20, −14.42 ppm(1:1 ratio of diastereomers).

EXAMPLE 17

5-Fluoro-2'-deoxy-5'-uridyl-[2-(4,4,6-trimethyltetrahydro-1,3-oxazin-yl)ethyl]-N-methyl-N-(2-chloroethyl)-phosphoramidate (1c)

This compound was prepared as described for 1a (0.32 mmol scale). The residue was purified by chromatography (3% MeOH:EtOAc) to afford 1c (51 mg, 28%): $R_f$ 0.43 (1:9 MeOH:$CH_2Cl_2$); $^1$H NMR ($CDCl_3$) 7.81(d, ½H, J=6.36 Hz), 7.72(d, ½H, J=6.39 Hz), 6.21(m, 1H), 4.51(m, 1H), 4,40 (m, 1H), 4.19(m, 5H), 3.76(m, 1H), 3.60(m, 2H), 3.33(m, 2H), 2.74(d, 3H, J=9.53 Hz), 2.45(m, 1H), 2.17(m, 1H), 1.91(m, 2H), 1.43(d, 1H, J=10.84 Hz), 1.06(m, 9H), 0.91(d, 1H, 12.30 Hz)ppm; $^{31}$P NMR ($CDCl_3$) −13.60, −13.78 ppm(mixture of diastereomers); IR (neat) 3400, 3180, 3080, 2960, 2920, 2900, 2820, 1710, 1660, 1470, 1400, 1355, 1345, 1320, 1260, 1200, 1180, 1160, 1090, 1030, 990, 975, 910, 870, 800, 735, 645 cm$^{-1}$; LSIMS m./e 557.3 (M+H)$^+$.

EXAMPLE 18

[2-(2,2-dimethyl-1,3-dioxolan-4-yl)ethyl]-N-methyl-N-(2-iodoethyl)phosphoramidoyl chloride (16c)

This compound was prepared using N-methyl-N-2-iodoethylamine.HI via N-methyl-N-(2-iodoethyl)phosphoramidic dichloride, as described for 16a (10 mmol scale). The crude product was purified by chromatography (1:4 EtOAc:hexanes) which afforded 16c as a pale yellow oil (2.50 g, 61%): $R_f$ 0.67 (1:1 EtOAc:hexanes); $^1$H NMR ($CDCl_3$) 4.27(m, 3H), 4.10(t, 1H, J=6.52 Hz), 3.59(t, 1H, J=7.38 Hz), 3.44(m, 2H), 3.26(t, 2H, J=7.56 Hz), 2.78(d, 3H, J=12.89 Hz), 2.00(dt, 2H, J=6.02 Hz), 1.38(d, 6H, J=15.48 Hz)ppm; $^{31}$P NMR ($CDCl_3$) −8.46, −8.69 ppm (1:1 ratio of diastereomers).

EXAMPLE 19

3'-O-t-Butyldimethylsilyl-5-fluoro-2'-deoxy-5'-uridyl-[2-(2,2-dimethyl-1,3-dioxolan-4-yl)ethyl]-N-methyl-N-(2-iodoethyl)phosphoramidate (17, X=I)

This compound was prepared as described for 17, X=Br (1.10 mmol scale) using 16c. The crude residue was purified by chromatography (EtOAc) to give 17, X=I (503 mg, 62%): $R_f$ 0.70 (1:9 MeOH:$CH_2Cl_2$); $^1$H NMR ($CDCl_3$) 7.80(d, ½H, J=6.30 Hz), 7.78(d, ½H, J=6.41 Hz), 6.22(dt, 1H, J=6.67 Hz), 4.39(m, 1H), 4.08(m, 7H), 3.53(m, 1H), 3.35(m, 2H), 3.21(m, 2H), 2.65(d, 3H, J=9.54 Hz), 2.29(m, 1H), 2.05(m, 1H), 1.93(m, 2H), 1.31(d, 6H, J=15.38 Hz), 0.83(s, 9H), 0.04(s, 6H)ppm; $^{31}$P NMR ($CDCl_3$) −14.39, −14.65 ppm (1:1 ratio of diastereomers).

EXAMPLE 20

3'-O-t-Butyldimethylsilyl-5-fluoro-2'deoxy-5'-uridyl-[2--(4,4,6-trimethyltetrahydro-1,3---oxazin-2-yl)ethyl]-N-methyl-N-(2-iodoethyl)phosphoramidate (18, X=I)

This compound was prepared as described for 18, X=Br (0.68 mmol scale). The crude residue was purified by chromatography (2% MeOH:EtOAc) to afford 18, X-I (166 mg, 32%): $R_f$ 0.73 (1:9 MeOH:$CH_2Cl_2$); $^1$H NMR ($CDCl_3$) 7.75(d, ½H, J=6.33 Hz), 7.71(d, ½H, J=6.25 Hz), 6.17(m, 1H), 4.33(m, 2H), 4.03(m, 5H), 3.66(m, 1H), 3.32(m, 2H), 3.22(m, 2H), 2.60(d, 3H, J=9.41 Hz), 2.26(m, 1H), 2.03(m, 1H), 1.87(m, 2H), 1.34(d, 1H, J=12.32 Hz), 1.08(m, 10H), 0.78 (s, 9H)ppm; $^{31}$P NMR ($CDCl_3$) −14.52, −14.77, −15.06, −15.31 ppm (mixture of diastereomers).

EXAMPLE 21

5-Fluoro-2'deoxy-5'-uridyl-[2-(4,4,6-trimethyltetrahydro-1,3-oxazin-2-yl)ethyl]-N-methyl-N-(2-iodoethyl)-phosphoramidate (1d)

This compound was prepared as described for 1a (0.22 mmol). The crude residue was purified by chromatography (3% MeOH:EtOAc) to afford 1d (40 mg, 28%): $R_f$ 0.34 (1:9 MeOH:$CH_2Cl_2$); $^1$H NMR ($CDCL_3$) 7.74(m, 1H), 6.18(m, 1H), 4.48(m, 1H), 4.45(m, 1H), 4.19(m, 5H), 3.72(m, 1H), 3.34(m, 2H), 3.26(m, 2H), 2.65(d, 3H, 9.36 Hz), 2.40(m, 1H), 2.14(m, 1H), 1.94(m, 2H), 1.44(d, 1H, 11.54 Hz), 1.12(m, 10H)ppm; $^{31}$P NMR ($CDCl_3$) −13.75, −14.04 ppm (1:1 ratio of diatereomers); IR (neat) 3380, 3050, 2960, 2920, 2820, 1710, 1660, 1465, 1400, 1355, 1320, 1260, 1240, 1275, 1090, 1030, 1000, 975, 940, 900, 870, 800, 735, 700 cm$^{-1}$; LSIMS calcd for MH$^+$. 649.1299; found 649.1315.

EXAMPLE 22

[2-(2,2-dimethyl-1,3-dioxolan-4-yl)ethyl]-morpholinophosphoramidoyl chloride (16d)

To a stirred solution of phosphorus oxychloride (17.63 g, 115 mmol) in $CH_2Cl_2$(100 ml) at 0° C. under $N_2$ was added morpholine (10.00 g, 115 mmol) in $CH_2Cl_2$ (30 ml). The mixture was allowed to stir overnight, under $N_2$, at room temperature. The mixture was poured over ice, the layers separated, and the aqueous layer extracted with $CH_2Cl_2$ (3×100 ml). The organic layers were combined, dried (MgSO$_4$), filtered, and the filtrate concentrated under reduced pressure. The residue was purified by chromatography (1:4 EtOAc:hexanes) to give morpholinophosphoramidic dichloride as a clear oil (16.04 g, 68%): R$_f$ 0.70 (1:4 EtOAc:hexane); $^1$H NMR (CDCl$_3$) 3.71(m, 4H), 3.30(m, 4H)ppm; $^{31}$P NMR (CDCl$_3$) −8.34 ppm; IR (neat) 2970, 2920, 2860, 1455, 1370, 1345, 1300, 1275, 1260, 1140, 1115, 1090, 1070, 1015, 970, 915, 850, 710 cm$^{-1}$.

16d was prepared using 24 as described for 16a (20 mmol scale). The crude residue was purified by chromatography (1:4 EtOAc:hexanes) to give 16d as a yellow oil (3.45 g, 55%): R$_f$ 0.54 (1:1 EtOAc:hexanes); $^1$H NMR (CDCl$_3$) 4.27(m, 2H); 4.16(m, 1H); 4.05(t, 1H, J=7.23 Hz), 3.67(m, 4H), 3.54(t, 1H, J=7.18 Hz), 3.13(m, 4H), 1.96(m, 2H), 1.32(d, 6H, J=16.36 Hz)ppm; $^{31}$P NMR (CDCl$_3$); IR(neat) 2980, 2920, 2850, 1710, 1455, 1370, 1330, 1300, 1275, 1260, 1215, 1160, 1140, 1110, 1095, 1055, 975, 920, 850, 715 cm$^{-1}$.

EXAMPLE 23

3'-O-t-Butyldimethylsilyl-5-fluoro-2'deoxy-5'-uridyl-[2-(2,2-dimethyl-1,3-dioxolan-4-yl)ethyl]-morpholinophosphoramidate (19)

This compound was prepared as described for (17 X=Br) (1.2 mmol scale). The crude residue was purified by chromatography (EtOAc) to give 19 (492 mg, 68%): R$_f$ 0.72 (1:9 MeOH:CH$_2$Cl$_2$); $^1$H NMR (CDCl$_3$) 7.76(d, ½H, J=6.31 Hz), 7.71(d, ½H, J=6.27 Hz), 6.22(m, 1H), 4.38(m, 1H), 4.06 (m, 6H), 3.88(m, 1H), 3.62(m, 4H), 3.54(5, 1H, J=7.00 Hz), 3.11(m, 4H), 2.25(m, 1H), 2.01(m, 1H), 1.88(m, 2H), 1.32(d, 6H, J=18.20 Hz), 0.84(s, 9H), 0.05(s, 6H)ppm; $^{31}$P NMR (CDCl$_3$) −16.15, −16.47 ppm (1:1 ration of diastereomers); LSIMS m/e 638(M+H)$^+$; 660(M+Na)$^+$.

EXAMPLE 24

3'-O-t-Butyldimethylsilyl-5-fluoro-2'deoxy-5'-uridyl-[2-(4,4,6-trimethyltetrahydro-1,3-oxazin-2-yl)ethyl]-morpholinophosphoramidate (20)

This compound was prepared as described for 18, X=Br (0.81 mmol scale) using 19. The crude product was purified by chromatography (2% MeOH:EtOAc) to give 20 (178 mg, 33%): R$_f$ 0.70 (1:9 MeOH:CH$_2$Cl$_2$); $^1$H NMR (CDCl$_3$) 7.78(d, ½H, J=6.15 Hz), 7.73(d, ½H, J=6.06 Hz), 6.23(m, 1H), 4.38(m, 2H), 4.07(m, 5H), 3.71(m, 1H), 3.63(m, 4H), 3.12(m, 4H), 2.27(m, 1H), 2.02(m, 1H), 1.89(m, 2H), 1.41(d, 1H, J=13.08), 1.07(m, 10H), 0.86(s, 9H), 0.06(s, 6H)ppm; $^{31}$P NMR (CDCl$_3$) −16.08, −16.39 ppm (1:1 ratio of diastereomers); IR (neat) 3400 2860, 2820, 2850, 1710, 1660, 1465, 1400, 1355, 1255, 1190, 1110, 1090, 1020, 975, 910, 830, 775 cm$^{-1}$.

EXAMPLE 25

5-Fluoro-2'-deoxy-5'-uridyl-[2-(4,4,6-trimethyltetrahydro-1,3-oxazin-2-yl)ethyl]-morpholinophosphoramidate (1e)

This compound was prepared as described for 1a (0.27 mmol scale). The crude residue was purified by chromatography (3% MeOH:EtOAc) to give 1e (65 mg, 44%): R$_f$ 0.36 (1:9 MeOH:CH$_2$Cl$_2$); $^1$H NMR (CDCl$_3$) 7.70(d, ½H, J=6.11 Hz), 7.64(d, ½H, J=6.13 Hz), 6.15(m, 1H), 4.40(m, 2H), 4.08(m, 5H), 3.70(m, 1H), 3.59(m, 4H), 3.08(m, 4H), 2.36(m, 1H), 2.02(m, 1H), 1.88(m, 2H), 1.39(d, 1H, J=13.04 Hz), 1.16(m, 10H)ppm; $^{31}$P NMR (CDCl$_3$) −15.42, −15.71, −15.83 ppm (mixture of diastereomers); IR (neat) 3400, 3080, 2960, 2850, 1710, 1650, 1470, 1450, 1400, 1350, 1260, 1100, 1030, 975, 910, 800, 730 cm$^{-1}$; LSIMS m/e 551(M+H)$^+$.

EXAMPLE 26

Preparation of Bis(2-bromoethyl)amine, hydrobromide salt

Ice cold diethanol amine (10 g, 95 mmol) was added dropwise to a stirred solution of hydrobromic acid (37.6 g, 464 mmol) at 0° C. The mixture was allowed to reflux and H$_2$O was distilled off at 1 hr intervals (26, 4, 4, 4, 4, 1, 1 ml). The mixture was refluxed for 3 hr, and then H$_2$O (29 ml) was distilled off. The yellow residue was poured into a beaker, while hot, containing acetone (30 ml). The product was allowed to crystallize out at 0° C. and isolated as a white solid (17.37 g, 59%); H NMR (DMSO-d$_6$) 3.72(t, 4H, J=6.70 Hz), 3.48(t, 4H, 6.73 Hz), 3.09(br.s, 1H)ppm.

EXAMPLE 27

Preparation of 3'-O-t-Butyldimethylsilyl thymidine 21

To a solution of thymidine (10.00 g, 41 mmol) in pyridine (50 ml) was added triphenylmethyl chloride (13.81 g, 50 mmol) and dimethylaminopyridine (0.4 g, 3.0 mmol). The mixture was allowed to stir at 80° C. for 30 min. The pyridine was removed under reduced pressure and the residue dissolved in DMF (80 ml). Imidazole (6.14 g, 90 mmol) and t-butyldimethylsilyl chloride (6.18 g, 41 mmol) were added, and the mixture was allowed to stir overnight at room temperature. The DMF was removed under reduced pressure, and the residue was dissolved in 80% aqueous acetic acid (60 ml). The mixture was allowed to reflux for 30 min, cooled, and neutralized with NaOH. The mixture was lyophilized, and the residue was purified by chromatography (1:1 EtOAc: hexanes) to give 21 as a white solid (10.35 g, 71%): mp 60° C. (softens), 90° C. (melts); R$_f$ 0.69 (1:9 MeOH:CH$_2$Cl$_2$); $^1$H NMR (CDCl$_3$) 7.33(m, 1H), 6.13(t, 1H, J=6.75 Hz), 4.48(m, 1H), 3.90(m, 2H), 3.74(m, 1H), 2.32(m, 1H), 2.22(m, 1H), 1.89(s, 3H), 0.88(s, 9H), 0.07(s, 6H)ppm.

EXAMPLE 28

Preparation of 3'-O-t-Butyldimethylsilyl-2'-deoxyuridine 22

To a solution of 2'-deoxyuridine (5.00 g, 22 mmol) in pyridine (20 ml) was added triphenylmethyl chloride (6.72 g, 24 mmol) and dimethylaminopyridine (0.20 g, 1.6 mmol). The mixture was allowed to stir at 80° C. for 30 min. The pyridine was removed under reduced pressure and the residue dissolved in DMF (30 ml). Imidazole (3.59 g, 53 mmol) and t-butyldimethylsilyl chloride (3.92 g, 26 mmol) were added, and the mixture was allowed to stir overnight at room temperature. The DMF was removed under reduced pressure, and the residue was dissolved in 80% aqueous acetic acid (20 ml). The mixture was allowed to reflux for 30 min, cooled, and neutralized with NaOH. The mixture was lyophilized, and the residue was purified by chromatography (1:1 EtOAc: hexanes) to give 22 as a white solid (3.13 g, 9.14 mmol, 41.51% yield): mp 140° C. (softens), 160°-170° C. (melts); R$_f$ 0.65 (1:9 MeOH:CH$_2$Cl$_2$); $^1$H NMR (CDCl$_3$) 7.62(d, 1H, J=6.87 Hz), 6.16(t, 1H, J=6.61), 5.73(d, 1H, J=5.70 Hz), 4.49(m, 1H), 3.93(m, 2H), 3.76(m, 1H), 2.30(m, 1H), 2.19(m, 1H), 0.89(s, 9H), 0.09(s, 6H)ppm.

EXAMPLE 29

Preparation of 3'-O-t-Butyldimethylsilyl thymidyl-[-2-(2,2-dimethyl-1,3-dioxolan-4-yl) ] N-methyl-N-(2-bromoethyl phosphoramidate (25)

Lithium diisopropylamide was prepared by adding butyllithium (5.50 ml, 11 mmol, 2.0M) to a stirred solution of diisopropylamine (1.54 ml, 11 mmol) in THF (1 ml) at 0° C. The mixture was allowed to stir at 0° C. for 10 min. This alkoxide solution was added dropwise to a stirred solution of 21 (1.77 g, 4.99 mmol) in the THF (8 ml) at 0° C. This alkoxide solution was then added dropwise to a stirred solution of 16a (2.00 g, 5.48 mmol) in THF (7 ml) at 0° C. and stirring was continued overnight at room temperature. The solvent was then removed under reduced pressure and the residue purified by chromatography (EtOAc) to give 25 (1.75 g, 51%): $R_f$ 0.75 (1:9 MeOH:$CH_2Cl_2$).

EXAMPLE 30

Preparation of 3'-O-t-Butyldimethylsilyl-2'-deoxy-5'-uridyl-[-2-(2,2-dimethyl-1,3-dioxolan-4-yl)]-N-methyl-N-(2-bromoethyl) phosphoramidate 26)

Lithium diisopropylamide was prepared by adding butyllithium (1.61 ml, 3.21 mmol, 2.0M) to a stirred solution of diisopropylamine (0.45 ml, 3.21 mmol) in THF (2 ml) at 0° C. The mixture was allowed to stir at 0° C. for 10 min. This solution was added dropwise to a stirred solution of 22 (0.500 g, 1.46 mmol) in THF (5 ml) at 0° C. This alkoxide solution was then added dropwise to a stirred solution of 16a (0.532 g, 1.46 mmol) in THF (6 ml) at 0° C. and stirring was continued overnight at room temperature. The solvent was then removed under reduced pressure and the residue purified by chromatography (EtOAc) to give 26 (718 mg, 73%): $R_f$ 0.75 (1:9 MeOH:$CH_2Cl_2$).

EXAMPLE 31

Preparation of 3'-O-t-Butyldimethylsilyl thymidyl-[2-(4,4,6-trimethyltetrahydro-1,3-oxazin-2-yl)ethyl]-N-methyl-N-(2-bromoethyl)phosphoramidate (27)

Compound 25 (1.72 g, 2.52 mmol) was dissolved in 80% aqueous acetic acid (7 ml), heated to 80° C. for 30 min, cooled, and neutralized with NaOH. The solution was lyophilized, the residue taken up in THF, the salts removed by filtration, and the residue concentrated under reduced pressure to afford the diol as an oil (1.00 g, 62%): $R_f$ 0.50 (1:9 MeOH:$CH_2Cl_2$); $^{31}$P NMR −13.97, −14.10 ppm (mixture of diastereomers). To a solution of the diol (855 mg, 1.30 mmol) in THF (3 ml) was added NaIO$_4$ (164 mg, 0.77 mmol) in acetate buffer (5 ml, 1M in $H_2O$, pH=5.0). The mixture was allowed to stir for 10 min, and the THF was then removed under reduced pressure. The mixture was lyophilized, the residue taken up in THF, the salts filtered, and the filtrate concentrated under reduced pressure. The residue was dissolved in $CH_2Cl_2$ (5 ml) and 4-amino-4-methyl-2-pentanol (125 mg, 1.06 mmol) in $CH_2Cl_2$ (3 ml) was added. The mixture was allowed to stir over 3Å molecular sieves for 10 min. The sieves were removed and the solvent removed under reduced pressure. The residue was purified by chromatography (2% MeOH:EtOAc) to give 27 (364 mg, 48%): $R_f$ 0.72 (1:9 MeOH: $CH_2Cl_2$).

EXAMPLE 32

Preparation of 3'-O-t-Butyldimethylsilyl-2'-deoxy-5'-uridyl-[2-(4,4,6-trimethyltetrahydro-1,3-oxazin-2-yl)ethyl]-N-methyl-N-(2-bromoethyl)phosphoramidate 28

Compound 26 (718 mq, 1.07 mmol) was dissolved in 80% aqueous acetic acid (3.5 ml), heated to 80° C. for 30 min, cooled, and neutralized with NaOH. The solution was lyophilized, the residue taken up in THF, the salts removed by filtration, and the residue concentrated under reduced pressure to afford the diol as an oil (440 mg, 65%): $R_f$ 0.53 (1:9 MeOH:$CH_2Cl_2$); $^{31}$P NMR −13.70, −13.90, −14.25 ppm (mixture of diastereomers). To a solution of the diol(440 mg, 0.70 mmol) in THF (3 ml) was added NaIO$_4$ (164 mg, 0.77 mmol) in acetate buffer (5 ml, 1M in $H_2O$, pH=5.0). The mixture was allowed to stir for 10 min, and the THF was then removed under reduced pressure. The mixture was lyophilized, the residue taken up in THF, the salts filtered, and the filtrate concentrated under reduced pressure. The residue was dissolved in $CH_2Cl_2$(5 ml) and the 4-amino-4-methyl-2-pentanol (82 mg, 0.70 mmol) in $CH_2Cl_2$ (3 ml) was added. The mixture was allowed to stir over 3 Å molecular sieves for 10 min. The sieves were removed and the solvent removed under reduced pressure. The residue was purified by chromatography (2% MeOH:EtOAc) to give 28 (203 mg, 42%): $R_f$=0.71 (1:9 MeOH:$CH_2Cl_2$).

EXAMPLE 33

Preparation of Thymidyl-[2-(4,4,-trimethyltetrahydro-1,3-oxazin-2-yl)ethyl]-N-methyl-N-(2-bromoethyl)phosphoramidate (7)

Tetrabutylammonium fluoride (0.48 ml, 0.48 mmol, 1.0M in THF) was added at 0° C. to a stirred solution of 27 (344 mg, 0.48 mmol) in THF (5 ml). The mixture was allowed to stir for 30 min at 0° C. The solvent was removed under reduced pressure and the residue purified by chromatography (3% MeOH:EtOAc) to give 7 (76 mg, 0.13 mmol, 26% yield): $R_f$=0.42 (1:9 MeOH:$CH_2Cl_2$); $^1$H NMR (CDCl$_3$) 7.39(m, 1H), 6.25(m, 1H), 4.53(m, 1H), 4.39(m, 1H), 4.15(m, 5H), 3.77(m, 1H), 3.43(m, 4H), 2.73(d, 3H, J=9.62 Hz), 2.41(m, 1H), 2.17(m, 1H), 1.98(m, 5H), 1.44(d, 1H, J=13.4 Hz), 1.13(m, 9H), 1.08(d, 1H, J=13.00 Hz)ppm.

EXAMPLE 34

Preparation of 2'-Deoxy-5'-uridyl-[2-(4,4,-trimethyltetrahydro-1,3-oxazin-2-yl)ethyl]-N-methyl-N-(2-bromoethyl)phosphoramidate (5)

Tetrabutylammonium fluoride (0.28 ml, 0.28 mmol, 1.0M in THF) was added at 0° C. to a stirred solution of 28 (193 mg, 0.28 mmol) in THF (2 ml). The mixture was allowed to stir for 45 min at 0° C. The solvent was removed under reduced pressure and the residue purified by chromatography (3% MeOH:EtOAc) to give 5 (24 mg, 15%): $R_f$=0.38 (1:9 MeOH:$CH_2Cl_2$); $^1$H NMR (CDCl$_3$) 7.66(m, 1H), 6.20(m, 1H), 5.74(d, 1H, J=6.89 Hz), 4.56(m, 1H), 4.41(m, 1H), 4.13(m, 5H), 3.56(m, 1H), 3.43(m, 4H), 2.72(d, 3H, J=9.51 Hz), 2.37(m, 1H), 2.07(m, 1H), 1.81(m, 2H), 1.79(d, 1H, J=15.58 Hz), 1.09(m, 10H).

EXAMPLE 35

Preparation of Bis(2-bromoethyl)phosphoramidic dichloride (29)

TEA (7.12 g, 70 mmol) was added dropwise to a stirred solution of bis(2-bromoethyl)amine hydrobromide (10.00 g, 32 mmol) and phosphorus oxychloride (4.91 g, 32 mmol) in $CH_2Cl_2$ (50 ml) at 0° C. under $N_2$. The mixture was allowed to stir overnight and then poured over ice. The layers were separated, and the aqueous layer was extracted with $CH_2Cl_2$ (3×50 ml). The organic layers were combined and dried ($MgSO_4$). The filtrate was concentrated under reduced pressure and the residue purified by chromatography (1:4 EtOAc: hexanes) to give 29 as an oil (3.86 g, 35%); $^1H$ NMR ($CDCl_3$) 3.70 (t, 4H, 6.73 Hz), 3.55 (t, 4H, 6.75 Hz)ppm.

EXAMPLE 36

Preparation of [2-(2,2-dimethyl-1,3-dioxolan-4-yl)ethyl]-bis-(2-bromoethyl)phosphoramidoyl chloride (30)

Butyllithium (6.57 ml, 13 mmol, 2.0M) was added dropwise at 0° C. to a stirred solution of 4-(2-hydroxyethyl)-2,2-dimethyl-1,3-dioxolane (1.75 g, 12 mmol) and a crystal of phenylazodiphenylamine indicator in THF (6 ml). The resulting solution was added dropwise at −78° C. to a stirred solution of 29 (4.16 g, 12 mmol) in THF (7 ml). The mixture was allowed to stir at −78° C. for 3 hr, at which time the purple mixture turned yellow. The mixture was warmed to room temperature and the solvent was removed under reduced pressure. The residue was purified by chromatography (1:4 EtOAc: hexanes) to give 30 as an oil (3.55 g, 65%): $R_f$ 0.74 (1:1 EtOAc: hexanes); $^1H$ NMR ($CDCl_3$) 4.33(m, 2H), 4.20(m, 1H), 4.11 (t, 1H, J=7.13 Hz), 3.56(m, 9H), 2.05(m, 9H), 2.05(m, 2H), 1.39(d, 6H, J=15.75 Hz)ppm.

EXAMPLE 37

Preparation of 3'-O-t-Butyldimethylsilyl-5-fluoro-2'-deoxy-5'-uridyl-[2-(2,2-dimethyl-1,3-dioxolan-4-yl)ethyl]-bis-(2-bromoethyl)phosphoramidate (31)

Lithium diisopropylamide was prepared by adding butyllithium (1.70 ml, 3.39 mmol, 2.0M) to a stirred solution of diisopropylamine (0.48 ml, 3.39 mmol) in THF (1 ml) at 0° C. The mixture was allowed to stir at 0° C. for 15 min. This solution was added dropwise to a stirred solution of 15 (500 mg, 1.54 mmol) in THF (5 ml) at 0° C. This alkoxide solution was then added dropwise to a stirred solution of 30 (704 mg, 1.54 mmol) in THF (5 ml) at 0° C. and stirring was continued overnight at room temperature. The solvent was then removed under reduced pressure and the residue purified by chromatography (EtOAc) to give 31 (931 mg, 81%): $R_f$ 0.70 (1:9 MeOH: $CH_2Cl_2$); $^1H$ NMR ($CDCl_3$) 7.68(m, 1H), 6.25(m, 1H), 4.46(m, 1H), 4.18(m, 7H), 3.57(m, 1H), 3.45(m, 8H), 2.30(m, 1H), 2.18(m, 1H), 1.92(m, 2H), 1.37(d, 6H, J=13.7 Hz), 0.89(s, 9H), 0.08(s, 6H)ppm.

EXAMPLE 38

Preparation of 3'-O-t-Butyldimethylsilylthymidyl-[2(2,2-dimethyl-1,3-dioxolan-4-yl)ethyl]bis-(2-bromoethyl)phosphoramidate (32)

Lithium diisopropylamide was prepared by adding butyllithium (2.00 ml, 4.00 mmol, 2.0M) to a stirred solution of diisopropylamine (0.56 ml, 4.00 mmol) in THF (1 ml) at 0° C. The mixture was allowed to stir at 0° C. for 15 min. This solution was added dropwise to a stirred solution of 21 (647 mg, 1.82 mmol) in THF (3 ml) at 0° C. This alkoxide solution was then added dropwise to a stirred solution of 30 (1.00 g, 2.18 mmol) in THF (5 ml) at 0° C. and stirring was continued overnight at room temperature. The solvent was then removed under reduced pressure and the residue purified by chromatography (EtOAc) to give 32 (972 mg, 69%): $R_f$ 0.71 (1:9 MeOH: $CH_2Cl_2$); $^1H$ NMR ($CDCl_3$) 7.34(m, 1H), 6.24(dt, 1H, J=6.36 Hz), 4.36(m, 1H), 4.06(m, 7H), 3.50(m, 1H), 3.40(m, 8H), 2.18(m, 1H), 2.07(m, 1H), 1.85(m, 5H), 1.28(d, 6H, J=14.49 Hz), 0.82(s, 9H), 0.02(s, 6H)ppm.

EXAMPLE 39

Preparation of 3'-O-t-Butyldimethylsilyl-2'-deoxy-5'-uridyl-[2-(2,2-dimethyl-1,3-dioxolan-4-yl)ethyl]-bis-(2-bromoethyl)-phosphoramidate (33)

Lithium diisopropylamide was prepared by adding butyllithium (1.60 ml, 3.21 mmol, 2.0M) to a stirred solution of diisopropylamine (0.45 ml, 3.21 mmol) in THF (1 ml) at 0° C. The mixture was allowed to stir at 0° C. for 15 min. This solution was added dropwise to a stirred solution of 22 (500 mg, 1.46 mmol) in THF (5 ml) at 0° C. This alkoxide solution was then added dropwise to a stirred solution of 30 (668 mg, 1.46 mmol) in THF (5 ml) at 0° C. and stirring was continued overnight at room temperature. The solvent was then removed under reduced pressure and the residue purified by chromatography (EtOAc) to give 33 (765 mg, 68%): $R_f$ 0.75 (1:9 MeOH: $CH_2Cl_2$).

EXAMPLE 40

Preparation of 3'-O-t-Butyldimethylsilyl-5-fluoro-2'-deoxy-5'-uridyl-[3,4-(dihydroxy)butyl]-bis-(2-bromoethyl)phosphoramidate (34)

Compound 31 (931 mg, 1.25 mmol) was dissolved in 80% aqueous acetic acid (5 ml), heated to 80° C. for 30 min, cooled, and neutralized with NaOH. The solution was lyophilized, the residue taken up in THF, the salts removed by filtration, and the residue concentrated under reduced pressure. The crude residue was purified by chromatography (3% MeOH:EtOAc) to give 34 (528 mg, 60%): $R_f$ 0.60 (1:9 MeOH: $CH_2Cl_2$).

EXAMPLE 41

Preparation of 3'-O-t-Butyldimethylsilylthymidyl-[3,4-(dihydroxy)butyl]-bis-(2-bromoethyl)phosphoramidate (35).

Compound 32 (1.41 g, 1.47 mmol) was dissolved in 80% aqueous acetic acid (3 ml), heated to 80° C. for 30 min, cooled, and neutralized with NaOH. The solution was lyophilized, the residue taken up in THF, the salts removed by filtration, and the residue concentrated under reduced pressure. The crude residue was purified by chromatography (3% MeOH:EtOAc) to give 35 (630 mg, 60%): $R_f$ 0.57 (1:9 MeOH: $CH_2Cl_2$); $^1H$ NMR ($CDCl_3$) 7.32(d, 1H, J=6.73 Hz), 6.15(m, 1H), 4.37(m, 1H), 4.17(m, 5H), 4.00(m, 1H), 3.85(m, 1H), 3.63(m, 1H), 3.44(m, 8H), 2.24(m, 1H), 2.16(m, 1H), 1.92(s, 3H), 1.78(m, 2H), 0.88(s, 9H), 0.09(s, 6H)ppm.

EXAMPLE 42

Preparation of 3'-O-t-Butyldimethylsilyl-2'-deoxy-5'-uridyl-[3,4-(dihydroxy)butyl]-bis-(2-bromethyl)phosphoramidate (36)

Compound 33 (765 g, 1.00 mmol) was dissolved in 80% aqueous acetic acid (5 ml), heated to 80° C. for 30 min, cooled, and neutralized with NaOH. The solution was lyophilized, the residue taken up in THF, the salts removed by filtration, and the residue concentrated under reduced pressure. The crude residue was purified by chromatography (3% MeOH:EtOAc) to give 36 (545 mg, 75%): $R_f$ 0.58 (1:9 MeOH: $CH_2Cl_2$).

EXAMPLE 43

Preparation of 5-Fluoro-2'-deoxy-5'-uridyl-[2-(4,4,6-trimethyltetrahydro-1,3-oxazin-2-yl)ethyl]bis-(2-bromoethyl)phosphoramidate (9)

To a stirred solution of 34 (255 mg, 0.36 mmol) in $CH_3CN$ (4.8 ml) was added aqueous HF (0.25 ml, 50% in $H_2O$). The mixture was allowed to stir for 1 hr and was then neutralized with NaOH. The solution was lyophilized, the residue taken up in THF, the salts removed by filtration, and the filtrate concentrated under reduced pressure to afford the triol (163 mg, 73%): $R_f$ 0.36 (1:9 MeOH: $CH_2Cl_2$). To a solution of the triol (163 mg, 0.26 mmol) in THF (3 ml) was added sodium periodate in aqueous acetate buffer (3 ml, pH=5.0, 1M). The mixture was allowed to stir for 7 min, and the THF was then removed under reduced pressure. The solution was lyophilized, the residue taken up in THF, the salts filtered, and the filtrate concentrated under reduced pressure. The residue was dissolved in $CH_2Cl_2$ (5 ml) and 4-amino-4-methyl-2-pentanol (31 mg, 0.26 mmol) in $CH_2Cl_2$ (3 ml) was added. The mixture was allowed to stir over 3 Å molecular sieves for 15 mins. The sieves were removed under reduced pressure. The residue was purified by chromatography (3% MeOH: EtOAc) to give 9 (17 mg, 10%): $R_f$ 0.47 (1:9 MeOH $CH_2Cl_2$).

EXAMPLE 44

Preparation of Thymidyl-[2-(4,4,6-trimethyltetrahydro-1,3-oxazin-2-yl)ethyl]bis-(2-bromoethyl)phosphoramidate (8)

To a stirred solution of 35 (667 mg, 0.90 mmol) in $CH_3CN$ (4.75 ml) was added aqueous HF (0.25 ml, 50% in $H_2O$). The mixture was allowed to stir for 1.5 hr and was then neutralized with KOH. The solution was lyophilized, the residue taken up in THF, the salts removed by filtration, and the filtrate concentrated under reduced pressure to afford the triol (393 mg, 70%): $R_f$ 0.33 (1:9 MeOH: $CH_2Cl_2$). To a solution of the triol (393 mg, 0.63 mmol) in THF (3 ml) was added sodium periodate in aqueous acetate buffer (3 ml, pH=5.0, 1M). The mixture was allowed to stir for 8 min, and the THF was then removed under reduced pressure. The solution was lyophilized, the residue taken up in THF, the salts filtered, and the filtrate concentrated under reduced pressure. The residue was dissolved in $CH_2Cl_2$ (4 ml) and 4-amino-4-methyl-2-pentanol (59 mg, 0.50 mmol) in $CH_2Cl_2$ (3 ml) was added. The mixture was allowed to stir over 3 Å molecular sieves for 10 mins. The sieves were removed under reduced pressure. The residue was purified by chromatography (3% MeOH: EtOAc) to give 8 (167 mg, 48%): $R_f$ 0.50 (1:9 MeOH: $CH_2Cl_2$); $^1H$ NMR ($CDCl_3$) 7.38(d, 1H J=15.55 Hz) 6.23(m, 1H) 4.50(m, 1H) 4.43(m, 1H), 4.19(m, 4H), 4.06(m, 1H), 3.79(m, 1H), 3.44(m, 8H), 2.64(m, 1H), 2.28(m, 1H), 1.93(m, 5H), 1.45(d, 1H, J=13.71 Hz), 1.15(m, 10H)ppm.

EXAMPLE 45

Preparation of 2'-Deoxy-5'-uridyl-[2-(4,4,6-trimethyltetrahydro-1,3-oxazin-2-yl)ethyl]-bis-(2-bromoethyl)phosphoramidate (6)

To a stirred solution of 36 (545 mg, 0.70 mmol) in $CH_3CN$ (4.75 ml) was added aqueous HF (0.25 ml, 50% in $H_2O$). The mixture was allowed to stir for 1.5 hr and was then neutralized with KOH. The solution was lyophilized, the residue taken up in THF, the salts removed by filtration, and the filtrate concentrated under reduced pressure to afford the triol (323 mg, 76%): $R_f$ 0.33 (1:9 MeOH: $CH_2Cl_2$). To a solution of the triol (323 mg, 0.53 mmol) in THF (3 ml) was added sodium periodate in aqueous acetate buffer (3 ml, pH=5.0, 1M). The mixture was allowed to stir for 10 min, and the THF was then removed under reduced pressure. The solution was lyophilized, the residue taken up in THF, the salts filtered, and the filtrate concentrated under reduced pressure. The residue was immediately dissolved in $CH_2Cl_2$(10 ml) and 4-amino-4-methyl-2-pentanol (62 mg, 0.53 mmol) in $CH_2Cl_2$ (5 ml) was added. The mixture was allowed to stir over 3 Å molecular sieves for 10 mins. The sieves were removed under reduced pressure. The residue was purified by chromatography (3% MeOH: EtOAc) to give 6 (120 mg, 33%): $R_f$ 0.53 (1:9 MeOH: $CH_2Cl_2$).

EXAMPLE 46

Preparation of 3'-O-t-Butyldimethylsilylthymidyl-[2-(2,2-dimethyl-1,3-dioxolan-4-yl)ethyl]-morpholinophosphoramidate (40)

Lithium diisopropylamide was prepared by adding butyllithium (2.1 ml, 4.20 mmol, 2.0M) to a stirred solution of diisopropylamine (0.58 ml, 4.20 mmol) in THF (1 ml) at 0° C. The mixture was allowed to stir at 0° C. for 10 min. This solution was added dropwise to a stirred solution of 21 (680 mg, 1.91 mmol) in THF (6 ml) at 0° C. This alkoxide solution was then added dropwise to a stirred solution of 16d (600 mg, 1.91 mmol) in THF (5 ml) at 0° C., and stirring was continued overnight at room temperature. The solvent was then removed under reduced pressure and the residue purified by chromatography (EtOAc) to give 40 (835 mg, 69%): $R_f$ 0.73 (1:9 MeOH: $CH_2Cl_2$).

EXAMPLE 47

Preparation of 3'-O-t-Butyldimethylsilyl-2'-deoxy-5'-uridyl-[2-(2,2-dimethyl-1,3-dioxolan-4-yl)ethyl]-morpholinophosphoramidate (41)

Lithium diisopropylamide was prepared by adding butyllithium (1.93 ml, 3.85 mmol, 2.0M) to a stirred solution of diisopropylamine (0.54 ml, 3.85 mmol) in THF (1 ml) at 0° C. The mixture was allowed to stir at 0° C. for 15 min. This solution was added dropwise to a stirred solution of 22 (600 mg, 1.75 mmol) in THF (5 ml) at 0° C. This alkoxide solution was then added dropwise to a stirred solution of 16d (550 mg, 1.75 mmol) in THF (5 ml) at 0° C., and stirring was continued overnight at room temperature. The solvent was then removed under reduced pressure and the residue purified by chromatography (EtOAc) to give 41 (556 mg, 51%): $R_f$ 0.70 (1:9 MeOH: $CH_2Cl_2$).

EXAMPLE 48

Preparation of 3'-O-t-Butyldimethylsilylthymidyl-[2-(4,4,6-trimethyltetrahydro-1,3-oxazin-2-yl)ethyl]morpholinophosphoramidate (42)

Compound 40 (835 mg, 1.32 mmol) was dissolved in 80% aqueous acetic acid in water (5 ml), heated to 80° C. for 30 min, cooled, and neutralized with NaOH. The solution was lyophilized, the residue taken up in THF, the salts removed by filtration, and the filtrate concentrated under reduced pressure to afford the diol (671 mg, 86%): $R_f$=0.56 (1:9 MeOH: $CH_2Cl_2$); $^{31}P$ NMR ($CDCl_3$) −15.53, −15.83 ppm (mixture of diastereomers). To a solution of the diol (671 mg, 1.13 mmol) in THF (4 ml) was added $NaIO_4$ (242 mg, 1.13 mmol) in aqueous acetate buffer (5 ml, pH=5.0, 1M). The mixture was allowed to stir for 7 min, and the THF was then removed under reduced pressure. The mixture was lyophilized, the residue taken up in THF, the salts filtered, and the filtrate concentrated under reduced pressure. The residue was dissolved in $CH_2Cl_2$ (3 ml), and 4-amino-4-methyl-2-pentanol (132 mg, 1.13 mmol) in $CH_2Cl_2$(3 ml) was added. The mixture was allowed to stir over 3 Å sieves for 15 min. The sieves were removed and the solvent removed under reduced pressure. The residue was purified by chromatography (2% MeOH: EtOAc) to afford 42 (404 mg, 54%): $R_f$ 0.70.

EXAMPLE 49

Preparation of 3'-O-t-Butyldimethylsilyl-2'-dioxy-5'-uridyl-[2-(4,4,6-trimethyltetrahydro-1,3-oxazin-2-yl)ethyl]-morpholinophosphoramidate (43)

Compound 41 (544 mg, 0.88 mmol) was dissolved in 80% aqueous acetic acid in water (3 ml), heated to 80° C. for 30 min, cooled, and neutralized with NaOH. The solution was lyophilized, the residue taken up in THF, the salts removed by filtration, and the filtrate concentrated under reduced pressure to afford the diol (417 mg, 82%): $R_f$=0.55 (1:9 MeOH: $CH_2Cl_2$); $^{31}P$ NMR ($CDCl_3$) −15.10, −15.25 ppm (mixture of diastereomers). To a solution of the diol (417 mg, 0.72 mmol) in THF (3 ml) was added $NaIO_4$ (154 mg, 0.72 mmol) in aqueous acetate buffer (3 ml, pH=5.0, 1M). The mixture was allowed to stir for 7 min, and the THF was then removed under reduced pressure. The mixture was lyophilized, the residue taken up in THF, the salts filtered, and the filtrate concentrated under reduced pressure. The residue was dissolved in $CH_2Cl_2$ (3 ml), and 4-amino-4-methyl-2-pentanol (84 mg, 0.72 mmol) in $CH_2Cl_2$ (3 ml) was added. The mixture was allowed to stir over 3 Å sieves for 15 min. The sieves were removed and the solvent removed under reduced pressure. The residue was purified by chromatography (2% MeOH: EtOAc) to afford 43 (154 mg, 33%): $R_f$ 0.70.

EXAMPLE 50

Preparation of Thymidyl-[2-(4,4,6-trimethyltetrahydro-1,3-oxazin-2-yl)ethyl]morpholinophosphoramidate (3)

Tetrabutylammonium fluoride (0.61 ml, 0.61 mmol, 1M in THF) was added at 0° C. to a stirred solution of 42 (404 mg, 0.61 mmol) in THF (3 ml). The mixture was allowed to stir for 20 min at 0° C. The solvent was removed under reduced pressure and the residue purified by chromatography (3% MeOH: EtOAc) to afford 3 (66 mg, 20%): $R_f$0.69 (1:9 MeOH: $CH_2Cl_2$); $^1H$ NMR ($CDCl_3$) 7.37(m, 1H), 6.25(m, 1H), 4.51(m, 1H), 4.38(m, 1H), 4.13(m, 5H), 3.70(m, 1H), 3.65(m, 4H), 3.15(m, 4H), 2.42(m, 1H), 2.17(m, 1H), 1.92(m, 5H), 1.43(d, 1H, J=13.08 Hz), 1.13(m, 10H)ppm; $^{31}P$ NMR ($CDCl_3$) −15.69, −15.82, −16.02 ppm (mixture of diastereomers); IR (thin film) 3400, 2960, 1690, 1470, 1370, 1250, 1110, 975 $cm^{-1}$.

EXAMPLE 51

Preparation of 2'-Deoxy-5'-uridyl-[2-(4,4,6-trimethyltetrahydro-1,3-oxazin-2-yl)ethyl]morpholinophosphoramidate (2)

Tetrabutylammonium fluoride (0.24 ml, 0.24 mmol, 1M in THF) was added at 0° C. to a stirred solution of 43 (154 mg, 0.24 mmol) in THF (2 ml). The mixture was allowed to stir for 20 min at 0° C. The solvent was removed under reduced pressure and the residue purified by chromatography (3% MeOH: EtOAc) to afford 2 (62 mg, 49%): $R_f$0.69 (1:9 MeOH: $CH_2Cl_2$); $^1H$ NMR ($CDCl_3$) 7.60(m, 1H), 6.25(m, 1H), 5.72(m, 1H), 4.51(m, 1H), 4.41(m, 1H), 4.15(m, 5H), 3.75(m, 1H), 3.67(m, 4H), 3.13(m, 4H), 2.45(m, 1H), 2.19(m, 1H), 1.93(m, 2H), 1.47(d, 1H, J=13.50 Hz), 1.14(m, 9H), 1.05(d, 1H, J=12.96 Hz) ppm; $^{31}P$ NMR ($CDCl_3$) −15.89, −16.08 ppm (1:1 ratio of diastereomers); IR (thin film) 3420, 2960, 2920, 1690, 1460, 1350, 1260, 1110, 1090, 975, 910, 810, 730 $cm^{-1}$; MS m/e 533(M+H)+, 555(M+Na)+.

EXAMPLE 52

Preparation of Piperidinophosphoramidic dichloride 44)

Triethylamine (18.25 g, 180 mmol) was added dropwise to a stirred solution of piperidine hydrochloride (10.00 g, 82 mmol) and phosphorus oxychloride (12.63 g, 82 mmol) in $CH_2Cl_2$ (100 ml) at 0° C. The mixture was allowed to stir overnight and then poured over ice. The layers were separated, and the aqueous layer was extracted with $CH_2Cl_2$(3×100 ml). The organic layers were combined and dried ($MgSO_4$). The filtrate was concentrated under reduced pressure and the residue purified by chromatography (1:4 EtOAc: hexanes) to give 44 (13.92 g, 84%): $R_f$0.70 (1:4 EtOAc: hexanes).

EXAMPLE 53

Preparation of [2-(2,2-dimethyl-1,3-dioxolan-4-yl)ethyl] piperidinophosphoramidate 45)

Butyllithium (11.00 ml, 22 mmol, 2.0M) was added dropwise at 0° C. to a stirred solution of 4-(2-hydroxyethyl)-2,2-dimethyl-1,3-dioxolane (2.92 g, 20 mmol) and a crystal of 4-phenylazodiphenylamine indicator in THF (7 ml). The resulting solution was added dropwise at −78° C. to a stirred solution of 44 (4.0 g, 20 mmol) in THF (5 ml). The mixture was allowed to stir at −78° C. for 3 hr, at which time the purple solution turned yellow. The mixture was warmed to room temperature and the solvent removed under reduced pressure. The residue was purified by chromatography (1:4 EtOAc: hexanes) to give 45 (2.69 g, 43%): $R_f$ 0.65 (1:4 EtOAc: hexanes).

EXAMPLE 54

Preparation of 3'-O-t-Butyldimethylsilyl-5-fluoro-2'-deoxy-5'-uridyl-[2-(2,2-dimethyl-1,3-dioxolan-4-yl)ethyl]-piperidinophosphoramidate (46)

Lithium diisopropylamide was prepared by adding butyllithium (0.96 ml, 1.91 mmol, 2.0M) to a stirred solution of diisopropylamine (0.27 ml, 1.91 mmol) in THF (1.0 ml) at 0° C. The mixture was allowed to stir at 0° C. for 15 min. This solution was added dropwise to a stirred solution of 15 (313 mg, 0.87 mmol) in THF (6 ml) at 0° C. This alkoxide solution was then added dropwise to a stirred solution of 45 (271 mg, 0.87 mmol) in THF (5 ml) at 0 ° C., and stirring was continued overnight at room temperature. The solvent was then removed under reduced pressure and the residue purified by chromatography (EtOAc) to give 46 (473 mg, 86%): $R_f$ 0.73 (1:9 MeOH: $CH_2Cl_2$).

EXAMPLE 55

Preparation of 3'-O-t-Butyldimethylsilyl-5-fluoro-2'-deoxy-5'-uridyl-[2-(4,4,6-trimethyltetrahydro-1,3-oxazin-2-yl)ethyl]-piperidinophosphoramidate (47)

Compound 46 (473 mg, 0.74 mmol) was dissolved in 80% aqueous acetic acid in water (5 ml), heated to 80° C. for 30 min, cooled, and neutralized with NaOH. The solution was lyophilized, the residue taken up in THF, the salts removed by filtration, and the filtrate concentrated under reduced pressure to afford the diol (368 mg, 83%): $R_f$=0.56 (1:9 MeOH: $CH_2Cl_2$); $^{31}P$ NMR ($CDCl_3$) −14.19, −14.54, −14.65, −14.74 ppm (mixture of diastereomers). To a solution of the diol (368 mg, 0.62 mmol) in THF (4 ml) was added $NaIO_4$ (132 mg, 0.62 mmol) in aqueous acetate buffer (4 ml, pH=5.0, 1M). The mixture was allowed to stir for 10 min, and the THF was then removed under reduced pressure. The mixture was lyophilized, the residue taken up in THF, the salts filtered, and the filtrate concentrated under reduced pressure. The residue was dissolved in $CH_2Cl_2$(3 ml), and 4-amino-4-methyl-2-pentanol (84 mg, 0.72 mmol) in $CH_2Cl_2$ (3 ml) was added. The mixture was allowed to stir over 3Å sieves for 15 min. The sieves were removed and the solvent removed under reduced pressure. The residue was purified by chromatography (2% MeOH: EtOAc) to afford 47 (67 mg, 17%): $R_f$ 0.70.

EXAMPLE 56

Preparation of 5-Fluoro-2'-deoxy-5'-uridyl-[2-(4,4,6-trimethyltetrahydro-1,3-oxazin-2-yl)ethyl]piperidinophosphoramidate (4)

Tetrabutylammonium fluoride (0.104 ml, 0.10 mmol, 1M in THF) was added at 020 C. to a stirred solution of 47 (67 mg, 0.10 mmol) in THF (2 ml). The mixture was allowed to stir for 20 min at 0° C. The solvent was removed under reduced pressure and the residue purified by chromatography (3% MeOH: EtOAc) to afford 4 (10 mg, 18%): $R_f$0.70 (1:9 MeOH: $CH_2Cl_2$); $^1H$ NMR ($CDCl_3$) 7.75(m, 1H), 6.21(m, 1H), 4.52(m, 1H), 4.42(m, 1H), 4.12(m, 5H), 3.71(m, 1H), 3.09(m, 4H), 2.42(m, 1H), 2.19(m, 1H), 1.91(m, 2H), 1.52(m, 6H), 1.41(d, 1H, J=12.96 Hz), 1.13(m, 10H)ppm; $^{31}P$ NMR ($CDCL_3$) −14.13, −14.36 ppm (1:1 ratio of diastereomers).

EXAMPLE 57

Biological Activity

A. Cytotoxicity against B16 Melanoma Cells

B16 cells in exponential growth (2–3×$10^6$ cells in 10 ml of serum-free MEM medium) were treated with drug for 2 hr. The cells were separated, washed, and resuspended in MEM medium supplemented with 10% fetal bovine serum. The cells were plated in 60-mm culture dishes at a density of 50–50,000 cells/plate (depending upon the drug concentration used initially) and then incubated for 8 days in a $CO_2$ incubator at 37° C. The colonies were fixed and stained with 0.5% crystal violet in ethanol and counted. The results are summarized in Table I above.

B. Cyctotoxicity Against L1210 Leukemia Cells

In addition to the B16 melanoma cell assay summarized in Table I, compounds 1a–e, 5 and 7 were evaluated for growth inhibitory activity against L1210 leukemia cells. Stock solutions of the compounds were prepared in 95% ethanol, and serial dilutions of drug were prepared in ethanol such that 50 μl of drug solution added to 10 ml of cell suspension gave the desired final concentration. L1210 cells in exponential growth were suspended in Fischer's medium supplemented with 10% horse serum, 1% glutamine, and 1% antibiotic-antimycotic solution to give 10-ml volumes of cell suspension at a final density of 3–6×$10^4$/ml. Appropriate volumes of the solutions of each compound were transferred to the cell suspensions, and incubation was continued for 2, 8, 24, or 48 hr. The cells were spun down, resuspended in fresh drug-free medium, and returned to the incubator, then counted with a Coulter Counter 48 hr after treatment with the compound. The results are summarized on Table III, below.

TABLE III

| Growth Inhibition of Phosphoramidates 1a–e Against L1210 Leukemia Cells in vitro[a] | | | | |
|---|---|---|---|---|
| | $IC_{50}$, nM Treatment Time, hr | | | |
| Compd | 2 | 8 | 24 | 48 |
| 1a | 120 | 50 | 18 | 2.5 |
| 1b | 160 | 60 | 19 | 2.5 |
| 1c | 300 | 160 | 25 | 3.5 |
| 1d | 190 | 75 | 6 | 2.0 |
| 1e | 15,000 | 5,000 | 900 | 150 |
| 5 | 20,000 | 8,200 | 1,300 | 425 |
| 7 | 13,000 | 10,500 | 7,000 | 590 |
| 5-Fluorouracil | 2,200 | 630 | 220 | 125 |

[a]Data represents an average of at least two experiments; L1210 cells were treated with compound for 2, 8, 24 and 48 hr. The drug-containing medium was removed, cells were washed, complete medium was added, and the cells were incubated for 48 hr total. Cell counts were obtained 48 hr after the start of treatment.

The bromo compound 1a was a potent inhibitor of cell proliferation using a 2 hr contact time. The inhibitory activity was completely blocked by addition of 5 μM thymidine, confirming that this compound was acting via inhibition of thymidylate synthetase. The potency of 1a increased with longer treatment times and was 1–2 orders of magnitude more potent than 5-FU using treatment times of 2, 8, 24, and 48 hr. Comparable inhibition was observed with the iodo and tosyl analogs.

The chloro analog 1c, whose phosphoramidate would be expected to have a slower rate of alkylation, was less potent than 1a, 1b, and 1d at shorter exposure times but equipotent in the 24- and 48-hour treatment groups. The relationship between potency and alkylating activity was confirmed by the synthesis and evaluation of the non-alkylating morpholino phosphoramidate 1e. It is interesting to note that 1e is comparable in potency to 5-FU at long treatment times; the activity of 1e is also completely reversed by addition of thymidine, suggesting that thymidylate synthetase also represents the target for this compound. Thus, 1e might be a prodrug for FdUMP; the intracellular cleavage of the morpholine substituent is presumably enzymatic, because the morpholinophosphoramidate derivative NucOP-(O)(NR$^2$R$^3$)(O$^-$) is stable to hydrolysis under physiologic conditions.

All patents, patent documents and publications cited herein are incorporated by reference herein. The invention has been described with reference to various specific and preferred embodiments and techniques. However, it should be understood that many variations and modifications may be made while remaining within the spirit and scope of the invention.

What is claimed is:

1. A compound of the formula:

wherein R$^1$ is H, F or (C$_1$–C$_4$)alkyl; R$^2$ is CH$_2$CH$_2$X wherein X is Cl, Br, I or p-toluenesulfonyl; R$^3$ is (C$_1$–C$_4$)alkyl or is the same as R$^2$, or wherein R$^2$ and R$^3$ taken together with the N-atom are a 5- or 6-membered heterocyclic ring which is aliphatic or aliphatic interrupted by a ring oxygen or a second ring nitrogen; R$^4$ is (4,4,6-trimethyltetrahydro-1,3-oxazin-2-yl)ethyl, and the pharmaceutically acceptable salts thereof.

2. The compound of claim 1 wherein R$^1$ is F.
3. The compound of claim 1 wherein R$^1$ is CH$_3$ or H.
4. The compound of claim 1 wherein R$^2$ is CH$_2$CH$_2$Br or CH$_2$CH$_2$I.
5. The compound of claim 4 wherein R$^3$ is CH$_3$.
6. The compound of claim 4 wherein R$^3$ is CH$_2$CH$_2$Br.
7. The compound of claim 1 wherein R$^2$ and R$^3$ taken together with the N atom are morpholino.
8. The compound of claim 1 wherein R$^2$ and R$^3$ taken together with the N atom are piperidinyl.
9. 5-Fluoro-2'-deoxy-5'-uridyl-[-2-(4,4,6-trimethyltetrahydro-1,3-oxazin-2-yl)ethyl]-N-methyl-N-(-2-bromoethyl)phosphoramidate.
10. 5-Fluoro-2'-deoxy-5'-uridyl-[-2-(4,4,6-trimethyltetrahydro-1,3-oxazin-yl)ethyl]-N-methyl-N-(2-chloroethyl)phosphoramidate.

* * * * *

UNITED STATES PATENT AND TRADEMARK OFFICE
CERTIFICATE OF CORRECTION

PATENT NO. : 5,233,031
DATED : August 3, 1993
INVENTOR(S) : Richard F. Borch et al.

It is certified that error appears in the above-identified patent and that said Letters Patent is hereby corrected as shown below:

Column 4, line 56, "t,zH" should read --t,2H,--.

Column 8, line 57, "ethy" should read --ethyl--.

Column 14, line 7, "(718mq," should read --(718 mg,--.

Column 17 line 12, "bromethyl" should read --bromoethyl--.

Column 21, line 62, "020" should read --0°--.

Signed and Sealed this

Twenty-ninth Day of March, 1994

Attest:

BRUCE LEHMAN

Attesting Officer

Commissioner of Patents and Trademarks